(12) United States Patent
Vulfov

(10) Patent No.: US 9,757,326 B2
(45) Date of Patent: Sep. 12, 2017

(54) HAIR REJUVENATING LOTION

(71) Applicant: Aleksandor Vulfov, Warminster, PA (US)

(72) Inventor: Aleksandor Vulfov, Warminster, PA (US)

(73) Assignee: ARCANA LLC, Warminster, PA (US)

( * ) Notice: Subject to any disclaimer, the term of this patent is extended or adjusted under 35 U.S.C. 154(b) by 433 days.

(21) Appl. No.: 14/522,315

(22) Filed: Oct. 23, 2014

(65) Prior Publication Data
US 2016/0113862 A1  Apr. 28, 2016

(51) Int. Cl.
| | |
|---|---|
| *A61K 36/185* | (2006.01) |
| *A61K 36/28* | (2006.01) |
| *A61K 36/489* | (2006.01) |
| *A61K 36/73* | (2006.01) |
| *A61K 8/97* | (2017.01) |
| *A61Q 5/00* | (2006.01) |
| *A61K 8/92* | (2006.01) |
| *A61K 8/20* | (2006.01) |
| *A61K 8/23* | (2006.01) |
| *A61K 8/36* | (2006.01) |
| *A61K 8/34* | (2006.01) |
| *A61Q 7/00* | (2006.01) |

(52) U.S. Cl.
CPC .................. *A61K 8/97* (2013.01); *A61K 8/20* (2013.01); *A61K 8/23* (2013.01); *A61K 8/345* (2013.01); *A61K 8/36* (2013.01); *A61K 8/922* (2013.01); *A61Q 5/002* (2013.01); *A61Q 7/00* (2013.01)

(58) Field of Classification Search
CPC .... A61K 36/185; A61K 36/28; A61K 36/489; A61K 36/73
See application file for complete search history.

(56) References Cited

U.S. PATENT DOCUMENTS

| | | | | |
|---|---|---|---|---|
| 6,605,296 | B1 * | 8/2003 | Stuckler | A61K 8/553 424/400 |
| 7,854,922 | B2 * | 12/2010 | Tanabe | A61K 8/0212 424/70.13 |
| 7,897,183 | B2 * | 3/2011 | Ge | A61K 8/97 424/725 |
| 7,964,222 | B2 * | 6/2011 | Fukuda | A61K 8/34 424/70.1 |
| 8,043,637 | B2 * | 10/2011 | Ge | A61K 8/97 424/725 |
| 8,101,211 | B2 * | 1/2012 | Chiba | A61K 8/97 424/401 |
| 8,501,162 | B2 * | 8/2013 | Barton | A61K 8/498 424/59 |
| 2011/0117218 | A1 * | 5/2011 | Schmidt | A61K 8/63 424/727 |

* cited by examiner

*Primary Examiner* — Chris R Tate

(57) ABSTRACT

A hair rejuvenating lotion applied to a user's hair to treat and relieve symptoms caused by seborrheic dermatitis. Through use of plant extracts and other supplemental active ingredients, the hair rejuvenating lotion restores hair to a healthy condition, retains color and prevents hair loss. The plant extracts included are from the genera *echinops, alchemilla, staphylea,* and *scorzonera,* as well as the plants *sophora japonica* and nettle. The other supplemental active ingredients include sulfur, ammonium chloride, lead acetate, and castor oil. The base of the hair rejuvenating lotion consists of distilled water, glycerin, and ethyl alcohol. The plant extracts from the genera *echinops, alchemilla, staphylea, scorzonera* are dissolved into the ethyl alcohol to create a tincture solution. The tincture solution is mixed with the distilled water, glycerin, sulfur, *sophora japonica* extracts, nettle extracts, ammonium chloride, and castor oil to form the hair rejuvenating lotion.

9 Claims, 6 Drawing Sheets

HAIR REJUVENATING LOTION

FIELD OF THE INVENTION

The present invention relates generally to a hair lotion. More specifically, the present invention relates to a hair lotion which treats seborrhea, rejuvenates hair, and restores the natural hair color of the user.

BACKGROUND OF THE INVENTION

Dryness, rashes, and eczema, and other symptoms of seborrheic dermatitis of the scalp affect a wide range of people. These conditions cause itching, dandruff, discoloration, and other discomforting, or possibly embarrassing, symptoms. While these conditions are generally temporary, people may seek treatment to reduce the itching, soreness, or embarrassment as a result of the condition. Traditionally, there have been numerous attempts for a cure or relief for these ailments, including shampoos, ointments, steroid creams, antifungal creams, or even anti-yeast medication. These traditional methods vary in effectiveness or only affect a few symptoms.

Therefore, it is an object of the present invention to provide a hair rejuvenating lotion where several symptoms can be relieved and treated with a single product. The hair rejuvenating lotion provides many beneficial topical constituents for treatment of these conditions. The topical constituents include anti-septic, anti-fungal, anti-bacterial, antistatic, anti-itch, anti-inflammatory, moisturizing, and hair color retention properties to treat and relieve the symptoms of seborrheic dermatitis. These topical constituents are provided through natural plant extracts from nettle and *sophorica japonica*; extracts from the plant genera: *enchinops, alchemilla, staphylea*, and *scorzonera*; ammonium chloride; lead acetate; sulfur; glycerin; and castor oil. The present invention seeks to combine these ingredients in a unique composition that will help rejuvenate the hair and scalp of the user.

DETAIL DESCRIPTIONS OF THE INVENTION

All illustrations of the drawings are for the purpose of describing selected versions of the present invention and are not intended to limit the scope of the present invention.

The present invention is for a hair rejuvenating lotion which provides benefits to users who suffer from dryness, eczema, rashes and seborrheic dermatitis of the scalp. The hair rejuvenating lotion makes use of active ingredients from plants to help relieve these issues and provide treatment of several different medical conditions of the scalp.

Figure 1:
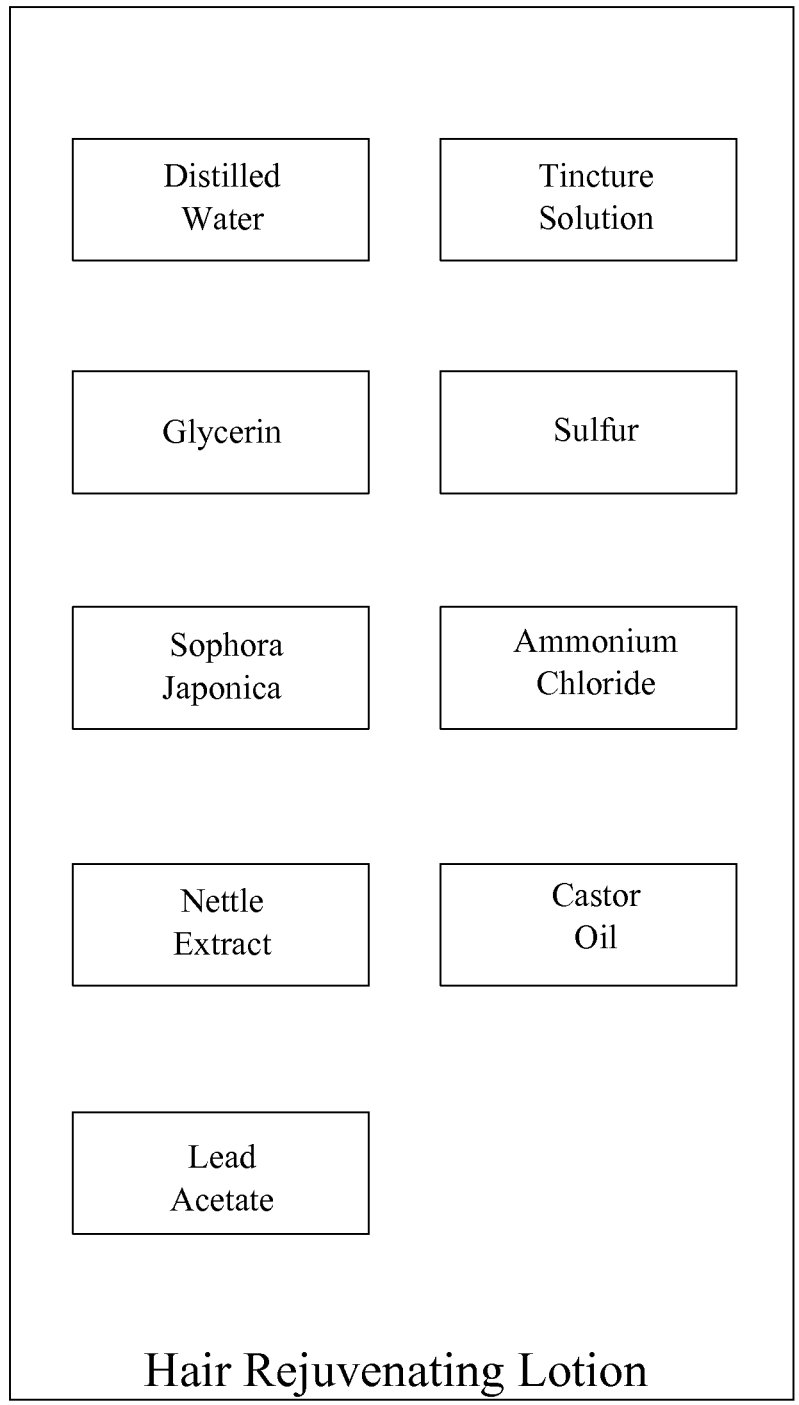
FIG. 1 is a block diagram of the ingredients of the present invention.
Figure 2:
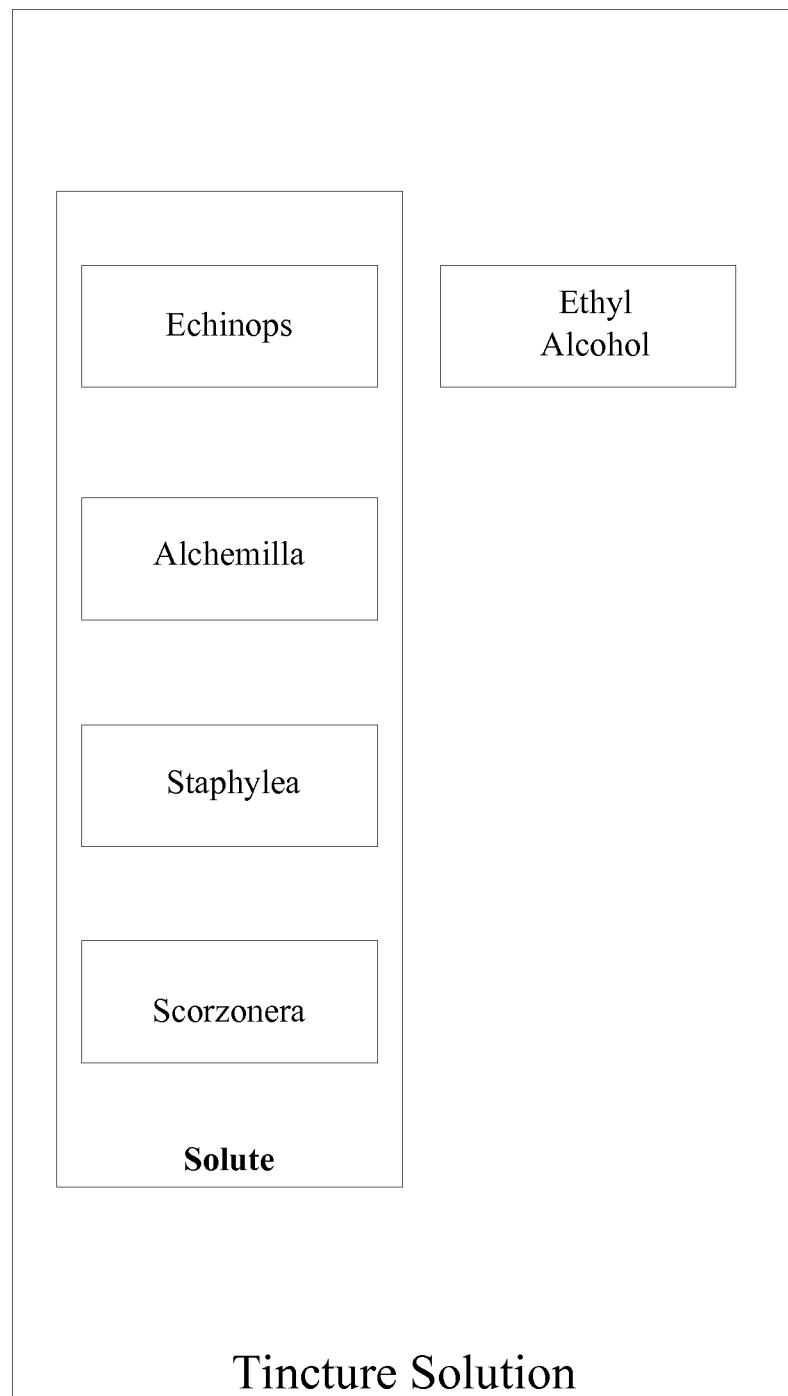
FIG. 2 is a block diagram of the ingredients of the tincture solution.

As presented in FIG. 1, the present invention comprises a mixture of distilled water, a tincture solution, glycerin, sulfur, nettle extract, *sophora japonica*, ammonium chloride, lead acetate, and castor oil. In accordance to FIG. 2, the tincture solution comprises a solute dissolved in ethyl alcohol. The solute comprises *echinops, alchemilla, staphylea* and *scorzonera*. The distilled water, glycerin, and ethyl alcohol are the base ingredients for the present invention. The distilled water provides a medium for the active components of the present invention to be suspended and fluid transportation properties to the mixture. The glycerin improves smoothness, provides lubrication for the lathering, and moisturizes the hair of the user as well as moisturizing their scalp. The ethyl alcohol provides an antiseptic, as well as a solvent of the tincture solution which the solute is dissolved within. The sulfur, nettle extract, *sophora japonica*, ammonium chloride, lead acetate, castor oil, *echinops, alchemilla, staphylea*, and *scorzonera* are supplemental yet active ingredients of the present invention. These active ingredients comprise a plurality of topically beneficial constituents.

In the preferred embodiment, the distilled water comprises about 78% by weight of the present invention. The distilled water accounts for most of the present invention to provide favorable fluid properties. The glycerin is about 7.5% by weight of the present invention, providing additional lubrication and preventing excess drying or evaporation. The sulfur is approximately 1.5% by weight of the present invention. The nettle extract comprises approximately 1% by weight of the present invention. The *sophora japonica* comprises about 1.6% by weight of the present invention. The ammonium chloride and the lead acetate each comprise approximately 0.4% by weight of the present invention. The castor oil comprises about 1.8% by weight of the present invention and the tincture solution comprises about 8% by weight of the present invention.

TABLE 1

Hair Rejuvenating Lotion

| Component | Approximate wt % |
|---|---|
| Distilled Water | 78 |
| Tincture Solution | 8 |
| Glycerin | 7.5 |
| Castor Oil | 1.8 |
| Sophora Japonica | 1.6 |
| Sulfur | 1.5 |
| Nettle Extract | 1 |
| Ammonium Chloride | 0.4 |
| Lead Acetate | 0.4 |

Figure 5:
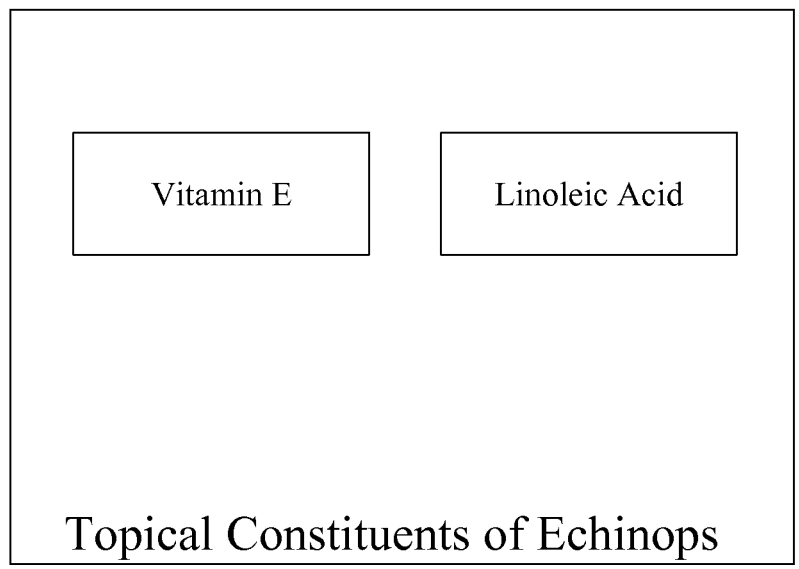
FIG. 5 is a block diagram of the topically beneficial constituents of the *echinops*.
Figure 6:
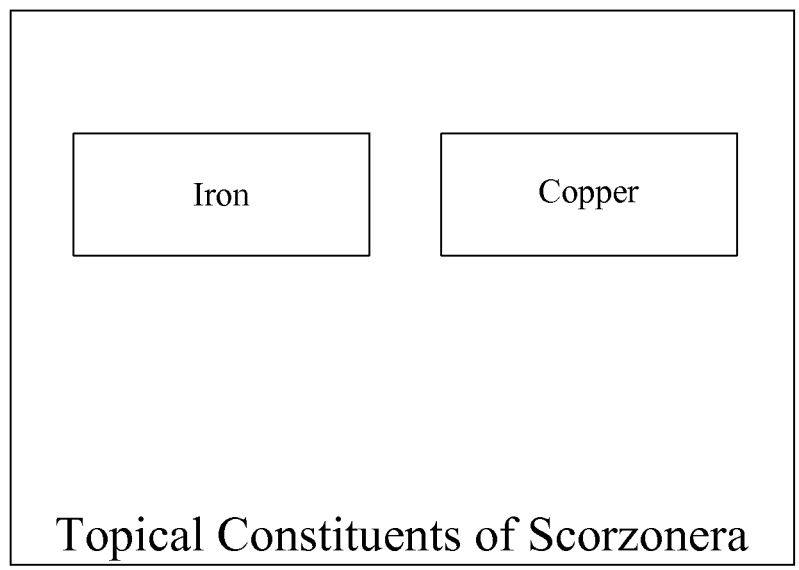
FIG. 6 is a block diagram of the topically beneficial constituents of the *scorzonera*.

The aforementioned *echinops, alchemilla, staphylea*, and *scorzonera* refer to latin plant genera, which the extracts are dissolved into the ethyl alcohol to form the tincture solution. The genera are referred to such that any plant extracts within the genera which provides similar beneficial topical constituents are within the scope of the present invention. In the preferred embodiment, the specific plants used from each genus are *echinops sphaerocephala, alchemilla caucasica, staphylea colchica*, and *scorzonera ketzhowelli*. The *echinops sphaerocephala* includes topically beneficial constituents of a high linoleic acid content and high vitamin E content, as shown in FIG. 5. The linoleic acid has antipruritic (anti-itch), anti-inflammatory, and moisture retentive properties, while the vitamin E content proves to keep hair healthy, promote hair growth and prevent hair loss. The *achemilla caucasica*, more commonly known as lady's mantle, helps to treat ulcers, eczema, and skin rashes. The *staphylea colchica* includes cytotoxic and antibacterial properties. The *scornonzera ketzhowelii* is rich in topically beneficial constituents containing a high content of copper and iron, as shown in FIG. 6. The copper helps to strengthen hair, intensify hair color, and prevent premature graying. The properties of the iron help to carry oxygen to the scalp. The *echinops, alchemilla, staphylea,* and *scorzonera* are mixed together in a ratio of 1:1:2:4, respectively, or the weight percents 12.5%, 12.5%, 25%, and 50%, respectively, as presented in Table 2.

TABLE 2

Solute Composition

| Component | Approximate wt % |
| --- | --- |
| Echinops | 12.5 |
| Alchemilla | 12.5 |
| Staphylea | 25 |
| Scorzonera | 50 |

Figure 3:
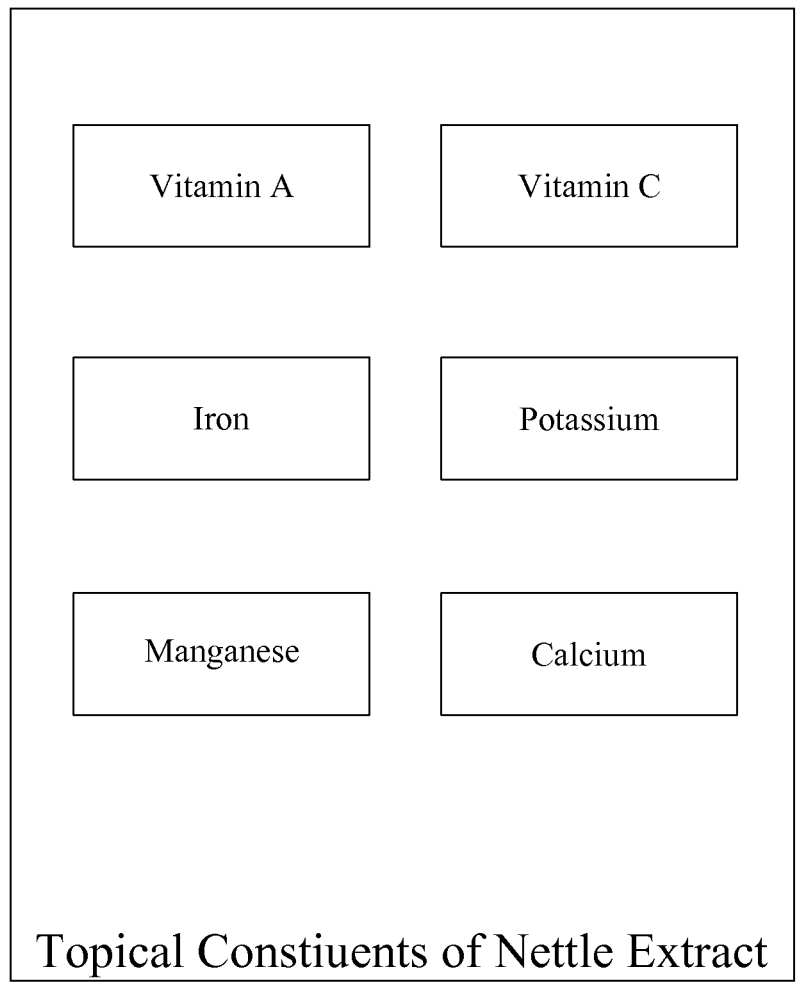
FIG. 3 is a block diagram of the topically beneficial constituents of the nettle extract.
Figure 4:
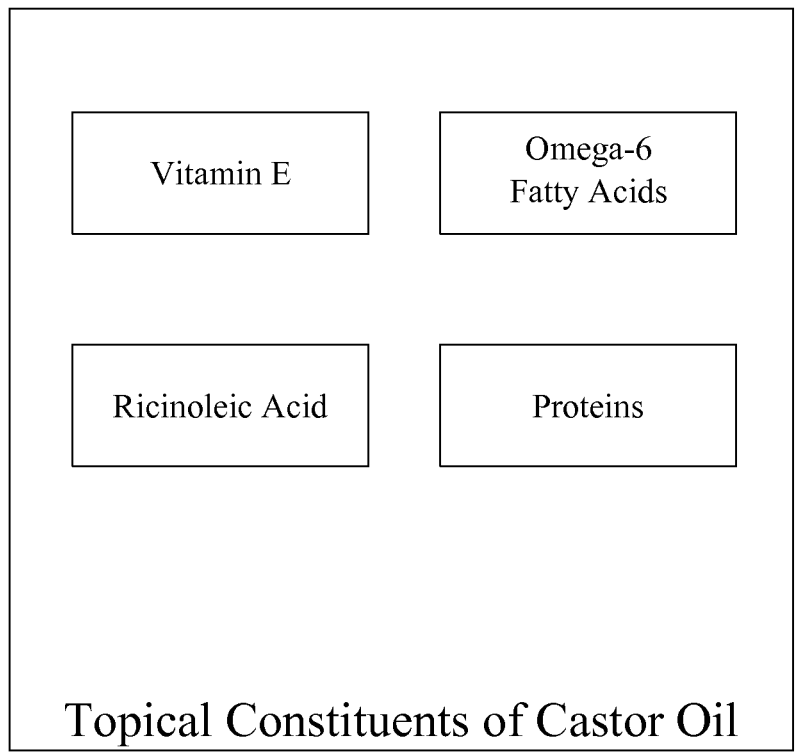
FIG. 4 is a block diagram of the topically beneficial constituents of the castor oil.

In addition to the tincture solution, the sulfur, nettle extract, *sophora japonica*, ammonium chloride, lead acetate, and the castor oil provide additional beneficial topical constituents to the present invention. The sulfur and the *sophora japonica* both provide additional antibacterial elements to the present invention. The nettle extract provides an additional source of iron as well as a high source of vitamin A, vitamin C, potassium, manganese, and calcium, as shown in FIG. 3. The nettle extract helps to control dandruff and help provide a shine to the user's hair. The inclusion of ammonium chloride provides the present invention with an antistatic effect. The lead acetate provides a color additive which, in addition to the sulfur, adjusts the color of the user's hair. The castor oil provides additional vitamin E and moisturizing properties to the present invention, as well as providing topically beneficial constituents: omega-6 fatty acid content, rincinoleic acid content, and protein content, as shown in FIG. 4. The castor oil helps to stimulate blood flow in the scalp, which in turn will help the wound or condition to heal more rapidly. The benefits of the nettle extract, castor oil, the *echinops*, and the *scorzonera* are topically applicable.

The present invention is applied daily to the hair and scalp of a user with seborrheic dermatitis. The daily consumption of the hair rejuvenating lotion it recommended to be approximately five to fifteen grams (5-15 g) depending on the hair type of the user. The present invention is applied to the user's hair using a hard toothbrush like comb applicator that distributes the hair rejuvenating lotion evenly across the user's hair and scalp. The follow through on the stroke with the applicator can remove any excess hair rejuvenating lotion from the user's hair.

Although the invention has been explained in relation to its preferred embodiment, it is to be understood that many other possible modifications and variations can be made without departing from the spirit and scope of the invention as hereinafter claimed.

What is claimed is:

1. A hair rejuvenation lotion comprising:
distilled water;
a tincture solution;
glycerin;
sulfur;
a nettle extract;
*sophora japonica;*
ammonium chloride;
lead acetate; and
castor oil,
wherein the tincture solution comprises a solute dissolved in ethyl alcohol,
wherein the solute comprises *echinops, alchemilla, staphylea,* and *scorzonera,*
wherein the distilled water is about 78% wt of the hair rejuvenation lotion,
wherein the glycerin is about 7.5% wt of the hair rejuvenation lotion,
wherein the sulfur is about 1.5% wt of the hair rejuvenation lotion,
wherein the nettle extract is about 1.0% wt of the hair rejuvenation lotion,
wherein the *sophora japonica* is about 1.6% wt of the hair rejuvenation lotion,
wherein the ammonium chloride is about 0.4% wt of the hair rejuvenation lotion,
wherein the lead acetate is about 0.4% wt of the hair rejuvenation lotion,
wherein the castor oil is about 1.8% wt of the hair rejuvenation lotion,
wherein the tincture solution is about 8.0% wt of the hair rejuvenation lotion,
wherein the *echinops* are about 12.5% wt of the solute,
wherein the *alchemilla* is about 12.5% wt of the solute,
wherein the *staphylea* is about 25% wt of the solute, and
wherein the *scorzonera* is about 50% wt of the solute.

2. The hair rejuvenation lotion as claimed in claim 1,
wherein the nettle extract comprises a plurality of topically beneficial constituents, and
wherein the plurality of topically beneficial constituents comprises a high vitamin A content, a high vitamin C content, a high iron content, a high potassium content, a high manganese content and a high calcium content.

3. The hair rejuvenation lotion as claimed in claim 1,
wherein the castor oil comprises a plurality of topically beneficial constituents, and
wherein the plurality of topically beneficial constituents comprises a vitamin E content, an Omega-6 essential fatty acid content, a ricinoleic acid content and a protein content.

4. The hair rejuvenation lotion as claimed in claim 1,
wherein the *echinops* comprises a plurality of topically beneficial constituents, and
wherein the plurality of topically beneficial constituents comprises a high linoleic acid content and a high vitamin E content.

5. The hair rejuvenation lotion as claimed in claim 1,
wherein the *scorzonera* comprises a plurality of topically beneficial constituents, and
wherein the plurality of topically beneficial constituents comprises a high iron content and a high copper content.

6. The hair rejuvenation lotion as claimed in claim 1,
wherein the distilled water, the ethyl alcohol and the glycerin are base ingredients in the hair rejuvenation lotion.

7. A hair rejuvenation lotion comprising:
distilled water;
a tincture solution;
glycerin;
sulfur;
a nettle extract;
*sophora japonica;*
ammonium chloride;

lead acetate; and
castor oil;
wherein the tincture solution comprises a solute dissolved in ethyl alcohol,
wherein the solute comprises *echinops, alchemilla, staphylea*, and *scorzonera,*
wherein the nettle extract, the castor oil, the *echinops* and the *scorzonera* each comprises a plurality of topically beneficial constituents,
wherein the distilled water being about 78% wt of the hair rejuvenation lotion,
wherein the glycerin being about 7.5% wt of the hair rejuvenation lotion,
wherein the sulfur being about 1.5% wt of the hair rejuvenation lotion,
wherein the nettle extract being about 1.0% wt of the hair rejuvenation lotion,
wherein the *sophora japonica* being about 1.6% wt of the hair rejuvenation lotion,
wherein the ammonium chloride being about 0.4% wt of the hair rejuvenation lotion,
wherein the lead acetate being about 0.4% wt of the hair rejuvenation lotion,
wherein the castor oil being about 1.8% wt of the hair rejuvenation lotion,
wherein the tincture solution being about 8.0% wt of the hair rejuvenation lotion,
wherein the *echinops* being about 12.5% wt of the solute,
wherein the *alchemilla* being about 12.5% wt of the solute,
wherein the *staphylea* being about 25% wt of the solute, and
wherein the *scorzonera* being about 50% wt of the solute.

8. The hair rejuvenation lotion as claimed in claim 7,
wherein the plurality of topically beneficial constituents of the nettle extract comprises a high vitamin A content, a high vitamin C content, a high iron content, a high potassium content, a high manganese content, and a high calcium content,
wherein the plurality of topically beneficial constituents of the castor oil comprises a vitamin E content, an Omega-6 essential fatty acid content, a ricinoleic acid content, and a protein content,
wherein the plurality of topically beneficial constituents of the *echinops* comprises a high linoleic acid content and a high vitamin E content, and
wherein the plurality of topically beneficial constituents of the *scorzonera* comprises a high iron content and a high copper content.

9. The hair rejuvenation lotion as claimed in claim 7,
wherein the distilled water, the ethyl alcohol and the glycerin are base ingredients in the hair rejuvenation lotion.

* * * * *